United States Patent
Brown

(10) Patent No.: US 11,291,405 B2
(45) Date of Patent: Apr. 5, 2022

(54) DETERMINING AND CONVEYING SLEEP FACTORS

(71) Applicant: HOWARD UNIVERSITY, Washington, DC (US)

(72) Inventor: Tyish S. Hall Brown, Laurel, MD (US)

(73) Assignee: HOWARD UNIVERSITY, Washington, DC (US)

( * ) Notice: Subject to any disclaimer, the term of this patent is extended or adjusted under 35 U.S.C. 154(b) by 193 days.

(21) Appl. No.: 16/338,082

(22) PCT Filed: Sep. 29, 2017

(86) PCT No.: PCT/US2017/054414
§ 371 (c)(1),
(2) Date: Mar. 29, 2019

(87) PCT Pub. No.: WO2018/064534
PCT Pub. Date: Apr. 5, 2018

(65) Prior Publication Data
US 2020/0022646 A1  Jan. 23, 2020

Related U.S. Application Data

(60) Provisional application No. 62/402,675, filed on Sep. 30, 2016.

(51) Int. Cl.
| | | |
|---|---|---|
| A61B 5/0205 | (2006.01) | |
| A61B 5/16 | (2006.01) | |
| A61B 5/00 | (2006.01) | |
| A61B 5/021 | (2006.01) | |
| A61B 5/024 | (2006.01) | |

(52) U.S. Cl.
CPC .......... *A61B 5/4812* (2013.01); *A61B 5/0205* (2013.01); *A61B 5/16* (2013.01); *A61B 5/486* (2013.01); *A61B 5/7425* (2013.01); *A61B 5/021* (2013.01); *A61B 5/024* (2013.01); *A61B 2560/0242* (2013.01); *A61B 2560/0252* (2013.01); *A61B 2562/0219* (2013.01)

(58) Field of Classification Search
CPC .......... A61B 2560/0242; A61B 5/1118; A61B 5/4806; A61B 5/4815; A61M 2205/3303; A61M 2205/3368; A61M 2205/3306
See application file for complete search history.

(56) References Cited

U.S. PATENT DOCUMENTS

| | | | | |
|---|---|---|---|---|
| 2014/0085077 A1* | 3/2014 | Luna | ............... | A61B 5/7455 340/539.11 |
| 2016/0151603 A1* | 6/2016 | Shouldice | ............... | H04R 3/00 600/28 |

* cited by examiner

*Primary Examiner* — Jon Eric C Morales
(74) *Attorney, Agent, or Firm* — Sughrue Mion, PLLC

(57) ABSTRACT

A system is configured to collect information regarding a user's sleep and to graphically convey sleep factors based on the information to a user. The system can include a control circuit and a sensor that work together configured to generate a first sleep factor. The first sleep factor is associated with the user's sleep episode. A database is communicatively coupled to the control circuit and stores a graphical representation of the user and a second sleep factor, which is defined by the user. The control circuit uses the first and second sleep factors to determine a sleep episode score. Optionally, the control circuit effects conveying the determined sleep episode score to the user via the graphical representation of the user.

17 Claims, 3 Drawing Sheets

DETERMINING AND CONVEYING SLEEP FACTORS

RELATED APPLICATION(S)

This application claims the benefit of U.S. Provisional Patent Application No. 62/402,675 filed Sep. 30, 2016, which application is incorporated by reference as though fully rewritten herein.

TECHNICAL FIELD

This invention relates generally to conveying sleep factors.

BACKGROUND

Sleep can be defined as a condition of body and mind that typically occurs for several hours every night, in which the nervous system is relatively inactive, the eyes closed, the postural muscles relaxed, and consciousness practically suspended. Obtaining optimal sleep can typically benefit immune function, metabolism, memory, learning, and/or other vital functions.

In certain embodiments, sleep episodes can refer to the total time spent in a sleep structure to engage in sleep. Sleep episodes can comprise one or more sleep cycles that include five stages or phases: stages 1, 2, 3, 4, and REM (rapid eye movement) sleep. Adults, for example, typically spend about 50 percent of their total sleep time in stage 2 sleep, about 20 percent in REM sleep, and the remaining 30 percent in stage 1, 3, and/or 4 sleep. Infants, by contrast, spend about half of their sleep time in REM sleep.

Stage 1 sleep typically refers to "light" sleep. For example, a person experiencing stage 1 sleep typically drifts in and out of sleep and can be awakened easily. Eye movement and muscle activity are slow (i.e., below a threshold value). People awakened from stage 1 sleep often remember fragmented visual images. Many also experience sudden muscle contractions called "hypnic myoclonia", and are often preceded by a sensation of falling.

Stage 2 sleep typically involves a cessation of eye movement (i.e., a lack of eye movement above a threshold value) and brain waves become slower (i.e., below a threshold value), with occasional bursts of rapid waves called "sleep spindles" that are 12-14 Hz waves that can occur for at least 0.5 seconds. During this stage heart rate slows and body temperature decreases. Stage 3 sleep typically involve brain waves that are about 1-8 Hz, called "delta waves", interspersed with smaller, faster waves. Stage 4 can typically involve delta waves almost exclusively. There is no statistically significant eye movement or muscle activity during stage 3 or 4 sleep. Stages 3 and 4 together are called "slow wave sleep" and are typically associated with, for example, tissue growth and repair, energy restoration, and hormone release. During REM sleep, breathing becomes more rapid, irregular, and shallow, significant eye movement occurs, heart rate and blood pressure increase, and limb muscles become temporarily paralyzed. REM sleep, for example, can provide energy to the brain and body as well as support daytime performance.

The first REM sleep period usually occurs about 70 to 90 minutes after the beginning of a night's sleep. A complete sleep cycle takes about 90 to 110 minutes on average. Psychologically beneficial sleep typically occurs as a result of completing a sleep cycle. Mental alertness and similar benefits of sleep may be reduced when a person awakens in the middle of a sleep cycle. Initial sleep cycles may contain relatively short REM periods and long periods of deep sleep. As the night progresses, REM sleep periods increase in length while deep sleep periods decrease in length. By morning, people spend nearly all their sleep time in stages 1, 2, and REM.

Humans, for example, spend about one-third of our lives sleeping. In addition to the benefits discussed above, sleeping can contribute to a healthy immune system, as well as help balance our appetites by helping to regulate levels of the hormone ghrelin and leptin, which play a role in our feelings of hunger and fullness. Although humans typically spend about a third of their lives sleeping, the recommended amounts of daily sleep varies with age. Table 1 is an exemplary illustration of recommended daily amounts of sleep in accordance with developmental need.

TABLE 1

| AGE | RECOMMENDED HOURS |
|---|---|
| 0-3 months | 14-17 |
| 4-11 months | 12-15 |
| 1-2 years old | 11-14 |
| 3-5 years old | 10-13 |
| 6-13 years old | 9-11 |
| 14-17 years old | 8-10 |
| 18-64 years old | 7-9 |
| ≥65 years old | 7-8 |

Unfortunately, many people do not engage in regular healthy sleep.

SUMMARY

Generally speaking, pursuant to these various embodiments, various methods and apparatuses are used to collect information regarding a user's sleep and provide feedback to the user regarding his or her sleep. The feedback can be graphical in nature to effectively engage the user to encourage better sleep habits. For example, teenagers often do not get the 8-10 hours of sleep that is recommended. To encourage better sleep habits, a graphical representation of the user can be used to illustrate to the teenager his or her sleep quality such as by showing an animation of the user being drowsy or clumsy after a poor night's sleep. On the other hand, the graphical representation can provide an energetic or happy animation of the user after a good night's sleep. In this way, encouragement to engage in better sleep habits can be realized through a gamification of the feedback.

In one example approach, a sensor is used to collect information regarding the user's sleep. This information is combined with other information unique to the user to determine a score for a given sleep episode for the user. The score is correlated to a particular graphical feedback that can be provided to the user via a smartphone, wearable fitness device, or the like to inform the user about his or her sleep quality and encourage improvement in sleep habits. These and other benefits can be realized through the study of the following description and figures.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Figure 1:
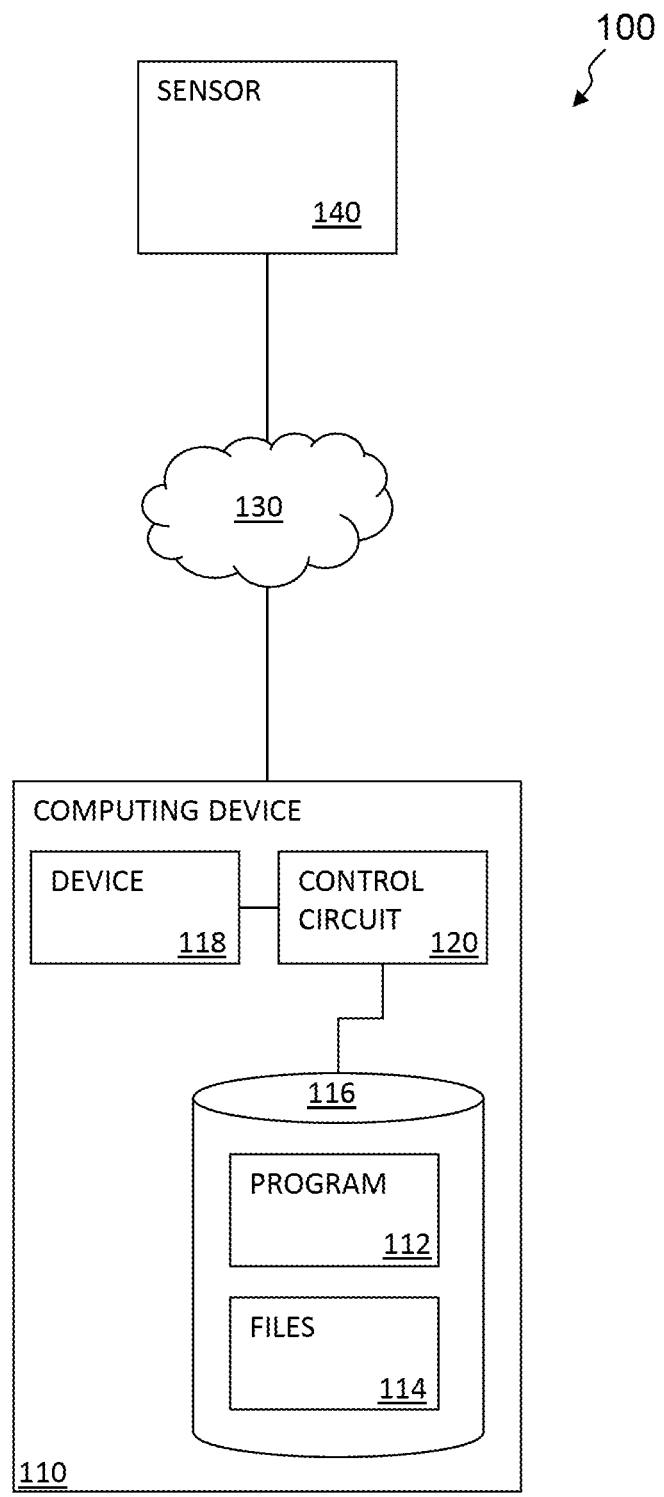
FIG. 1 illustrates a simplified block diagram of a system to convey sleep factors to users, in accordance with some embodiments.

Referring now to the drawings, in particular FIG. 1, an example system 100 for determining and conveying sleep factors is illustrated as a simplified block diagram. The system 100 includes one or more sensors 140 configured to collect information associated with a sleep episode of a user. The illustrated sensor 140 may include one or more devices that can capture various information or data are associated with user's sleep episodes, such as sleep quantity, heart rate, respiratory activity, body movement (e.g., eye, head, and/or limb movement), body temperature, room temperature, ambient sound, ambient light, electrophysiological activity, blood pressure, similar sleep factors, or a combination of two or more of the aforementioned sleep factors. Sensors 140 can be wearable computing devices that include headbands, wrist bands, watches, jewelry, shirts, pants, undergarments, similar apparel, or combinations of two or more of the aforementioned apparel items.

Additionally or alternatively, sensors 140 can be configured to attach to beds, pillows, covers, sheets, similar sleep-related items, or a combination of two or more of the aforementioned sleep-related items. For example, sensors 140 can be further configured to capture images and/or video (e.g., to determine body movement), capture thermographic images (e.g., to measure ambient temperature values), include one or more accelerometers (e.g., to capture body movement data), similar functionalities, or two or more of the aforementioned functionalities. Additionally or alternatively, sensors 140 can be configured to include one or more electrodes (e.g., to capture electroencephalogram data), monitor breathing movements in the chest and/or abdomen, emit and capture wireless signals to measure heart rate (e.g., via photoplethysmography, which determines heart rate via illuminating the skin surface and measuring changes in light absorption), generate geospatial data that reflects user location, similar functionalities, or two or more of the aforementioned functionalities. Sensor 140, for example, can comprise or be associated with a desktop computer, laptop computer, a thin client, a smart TV (e.g., to monitor users that fall asleep watching television), an in-vehicle computing device (e.g., to monitor users that sleep during travel), a wearable computing device, or a mobile device, including but not limited to, smart phones, phablets, tablets, or similar output devices.

A control circuit 120 of a computing device 110 is in communication with one or both of the sensor 140 and a database 116. In FIG. 1, the control circuit 120 communicates with the sensor 140 via one or more communication networks 130, which can be, for example, a local area network (LAN), a wide area network (WAN) such as the Internet, or a combination of the two, and includes wired, wireless, or fiber optic connections. In general, network 130 can be any combination of connections and protocols that can support communications between sensors 140 and computing devices 110, in accordance with some embodiments. The database 116 is configured to store a second sleep factor and a graphical representation of the user, for example, in files 114 located in the database. In this example, the second sleep factor is associated with the sleep episode and defined by the user.

The second sleep factor can be determined using a variety of information received from the user. For example, the second sleep factor can be determined based on information received from a user in response to sleep-related ecological momentary assessment ("EMA") questions. EMA questions solicit data that may be collected on a recurrent basis and is associated with a user's sleep patterns, sleep quality, environmental factors, social factors, individual factors, individual moods, stress levels, anxiety levels, or a combination of two or more thereof. For example, control circuits 120, invoking programs 112, can access one or more EMA questions included in files 114, convey the accessed EMA questions to the user via device 118 and prompt the user to respond accordingly. In certain embodiments, EMA questions may include a first question set that prompts users to rate one or more of the following sleep-related matters on a scale of zero (no issues or the highest satisfied) to four (the most issue or lowest satisfaction): difficulty falling asleep; difficulty staying asleep; problems waking up too early; level of satisfaction with their current sleep patterns, the extent to which the user has issues with their sleep problem, the extent to which their sleep problem is interfering with their daily functioning, similar questions related sleep, individual moods, stress levels, and/or anxiety levels, or a combination of two or more of the aforementioned questions.

In certain aspects, EMA questions may include a second question set that include one or more of the following sleep-related polar questions: user was fearful of letting their guard down while sleeping; user tries to stay as alert as possible while lying in bed; user is fearful of the loss of control they experience during sleep; user awoke from sleep and was terrified of returning to sleep; user avoids going to sleep because they thought that they would have really bad dreams; user awoke in the middle of the night from a nightmare and avoided going back to sleep because the nightmare may return; user is afraid to close their eyes; user feels that sleep is dangerous; user feels vulnerable when asleep; user avoids sleep; users focuses on strange noises when going to sleep; user is scared of the dark; user feels safer when sleeping with the light on, similar sleep-related polar questions, or a combination of two or more thereof.

User defined sleep factors that can be collected and considered as part of determining the second sleep factor, for example, may further include user sleep log data that includes a user's sleeping and waking times with related information, self-reported and/or third-party recorded information, one or more sleep charts demarcated by date and time, desired wake and/or sleep times, self-reported environmental disturbances, mental alertness characterizations, ingested pharmaceuticals associated with one or more sleep episodes, perceived stress information, perceived causes of nocturnal disturbances, similar sleep-related questions that can be used to quantify sleep episode quality, or a combination of two or more of the aforementioned data types.

Referring again to FIG. 1, the control circuit 120 is configured to generate a first sleep factor based at least in part on the information collected by the sensor 140 associated with the sleep episode and determine, using the first sleep factor and the second sleep factor, a sleep episode score. The control circuit 120 is further configured to effect conveyance of the sleep episode score to the user via display of the graphical representation of the user. In the example of FIG. 1, the control circuit 120 is operatively connected to a device 118 configured to provide an output to the user. In certain embodiments, device 118 is a multi-function device. In other approaches, device 118 can be an I/O device that conveys data in visual form and/or allows users to input data associated with user-defined sleep factors or in response to EMA questions. For example, device 118 can comprise one or more displays, keyboards, mice, microphone, virtual reality headset, gesture-based input devices, similar I/O devices, or a combination of two or more I/O devices. In some embodiments, device 118 can comprise a cathode ray tube display, light-emitting diode display, electroluminescent display, electronic paper, plasma display panel, liquid crystal display, organic light-emitting diode, a swept-volume display, varifocal mirror display, emissive volume display, laser display, holographic display, light field display, and other suitable display technologies.

The database 116 can be any memory device configured to store various information including programming information 112 and/or other data in files 114. For example, the stored data can include sleep factor data captured by sensors 140, user-defined sleep factor data (discussed further below), user-defined sleep structure (e.g., beds, couches, hammocks, and similar structures that facilitate sleep) location data, user age information, user gender information, user weight information, historic sleep factor data, the data of Table 1, a plurality of graphic icon visual states (discussed further below), sleep-related EMA questions, similar sleep factor data, or a combination of two or more of the aforementioned data types. The data may also include a plurality of unique graphical icons of which one or more may be utilized by the control circuit 120 to effect conveyance of a particular sleep factor, sleep efficiency data (i.e., the portion of a sleep episode actually filled by sleep), sleep episode durations, similar sleep factors, or a combination of two or more thereof. Graphical icons may include pixelated images of the user, two-dimensional images of the user, three-dimensional images of the user, whole body images of the user, bust images of the user, similar images, or a combination of two or more of the aforementioned images.

Figure 3:
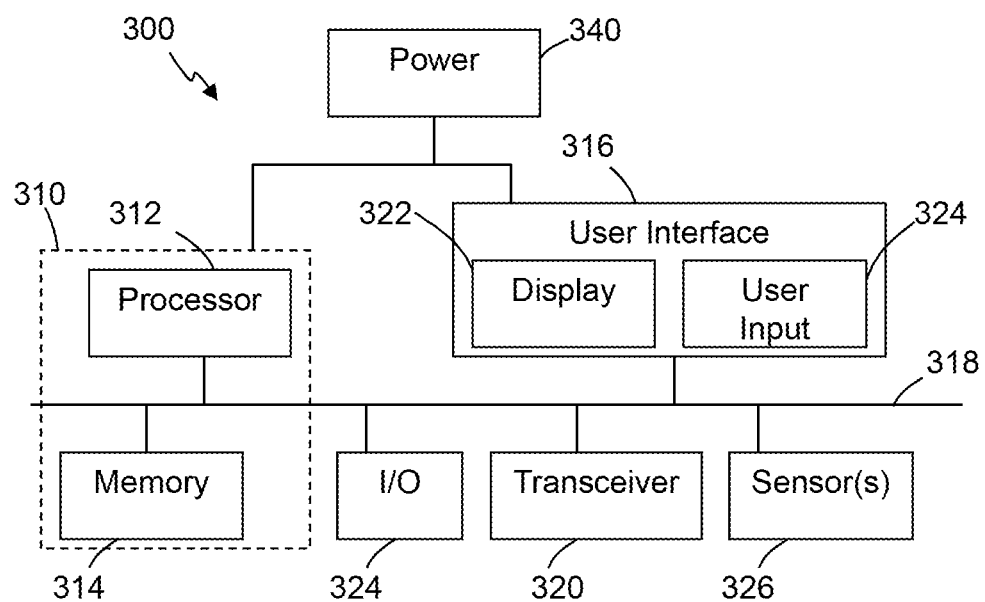
FIG. 3 illustrates an exemplary system for use in implementing methods, techniques, devices, apparatuses, systems, servers, sources and conveying sleep factors to users, in accordance with some embodiments.

Although illustrated in FIG. 1 as separate devices, in certain embodiments, sensors 140 and computing devices 110 can be integrated into a single unit such as in the form illustrated in FIG. 3. Similarly, the display device 118 can be integral with or separate from the computing device 110, control circuit 120, and/or the sensor 140. In practice, users can use the system to track, quantify, and/or monitor their sleep factors, improve the perceived satisfaction of their sleep episodes, similar sleep-related foci, or a combination of two or more of the aforementioned endeavors. So configured, an apparatus or system in accord with these teachings can track, quantify, and/or monitor one or more sleep activities (e.g., sleep duration, sleep cycles, REM sleep segments, one or more sleep stages), improve a user's perceived satisfaction of sleep episodes, improve a user's sleep hygiene, help a user take notice of similar sleep-related foci, or a combination of two or more thereof.

For instance, sleep episode scores can convey the efficiency of sleep episodes (e.g., the percent of a particular sleep episode actually spent sleeping). A sleep episode of about 85% is ideal and greater than 90% is above average. The one or more control circuits 120, invoking one or more programs 112, can use sleep factor data included in files 114 to quantify sleep episodes, quality sleep episodes, quantify the efficiency of user sleep episodes, perform similar sleep episode calculations, or a combination of two or more of the aforementioned sleep episode calculations.

For example, accelerometer data can quantify sleep episodes (e.g., a lack of movement above a threshold amount for a predetermined time period can denote a sleep episode). Heart rate data can confirm that a user is experiencing a sleep episode (i.e., heart rate values determined to be below a threshold amount for a predetermined time period can denote a sleep episode). The control circuit 120 can determine that a user is conscious using a variety of data such as heart rate values determined to be above a threshold amount for a predetermined time period can denote that the user is conscious and not asleep.

Additionally or alternatively, geolocation data reflecting the user's instant location can confirm that the user may be experiencing a sleep episode (i.e., user's instant location determined to be proximate to a user-defined sleep structure for a threshold time period can denote that the user is likely experiencing a sleep episode). In still another example, the sensor 140 can include a camera to capture one or more images and/or video to detect eye movement above a threshold amount to determine that the user may be in REM sleep and/or finishing a sleep cycle. The control circuit 120 in another approach can determine when a user is likely asleep by determining that the captured user's respiration rate included in files 114 is below a threshold value.

The sleep factors included in files 114 can be processed to determine sleep episode scores. For example, sleep episode scores, in some embodiments, can be binary (e.g., "yes" or "no"), percent-based (e.g., 25%, 50%, 75%, 100%, and any values therein), norm referenced, criterion-referenced, a similar performance conveying information type, or a combination of two or more of the aforementioned performance conveying information types. For example, the control circuit 120 can use accelerometer data, geolocational data, respiratory data, heart rate data, and/or EEG data stored in files 114 to determine that a 12 year old user was positioned proximate to a user-defined sleep structure (i.e., a bed) in a supine position, during which the user exhibited no movement above a threshold amount for 8.5 hours, with a respiration determined to be below a threshold amount which can reflect that the user experienced an 8.5 hour sleep episode.

The control circuit 120 can further access the age-related sleep episode recommendations (which are reflected in Table 1) included in files 114 and determine that the 12-year-old user 8.5-hour sleep episode reflects an accrual of about 94% of the recommended 9 hours (i.e., a sleep episode score of 94%). For instance, associated accelerometer data reflects a total of 52 minutes of movement above a threshold amount for a threshold time period. Thus, a control circuit 120 can further determine that the 12-year-old user was asleep for 7.63 hours out of a total of 8.5 hours, which denotes a sleep efficiency of about 89.8% (i.e., a sleep score of 94%). In certain instances, the system can further utilize one or more user-defined sleep factor data points, included in files 114, to further process determined sleep episode scores. For example, sleep episode scores can be reduced by a predetermined amount (i.e., a percent or absolute value) for each EMA question scored as a 3 or 4 included in the first question set (e.g., user has difficulties staying asleep, user has issues with difficulties falling asleep) and/or each affirmative answer for EMA questions included in the second question set (e.g., user avoids sleep, user feels that sleep is dangerous).

In the same vein, control circuit 120 typically does not amend sleep episode scores when first question set answers comprise a 1 or 2 and/or a second question set answer comprises a non-affirmative answer (e.g., user does not avoid sleep, user feels that sleep is not dangerous).

Sleep episode scores can be conveyed using graphical icons that resemble the user. In certain embodiments, one or more control circuits 120, invoking one or more programs 112, can visually convey generated sleep episode scores to users by, for example, accessing the user's generated sleep episode score included in files 114, determine the one or more unique graphical icons, included in files 114, that are associated with the generated sleep episode score, and convey the determined unique graphical icons to device 118 for presentation to the user. In instances where a plurality of unique graphical icons are employed to convey generated sleep episode scores, the determined unique graphical icons may be presented at a predetermined synchronous rate to convey motion. Examples include generating one or more user graphical icons by pixelating one or more images of the user (e.g., convert the image such that the pixel size of individual pixels are visible), converting a three-dimensional image of users to a two-dimensional caricature thereof, using similar image conversion methods, or two or more of the aforementioned image conversion methods. One or more images of users can be captured via sensors 140 and used to generate user graphical icons as discussed above.

Additionally or alternatively, control circuit 120 can animate one or more limbs, eyes, and/or facial expressions of the unique graphical icons to further convey sleep episode scores. Unique graphical icons may illustrate a user's full body, head, as well as head and upper torso. In some embodiments, files 114 can comprise one or more unique graphical icons that can be utilized to reflect a particular STATE (e.g., 1, 2, 3, 4, first, second, third, alpha, beta, gamma, and similar values), wherein each STATE can reflect a particular sleep episode score or range of sleep episode scores. Table 2 depicts an exemplary scheme that associates STATES with sleep episode scores.

TABLE 2

STATE 1 <75%
75% ≤ STATE 2 < 85%
85% ≤ STATE 3 < 95%
95% ≤ STATE 4

Hence, using Table 2 as a guide, the 94% sleep episode score discussed above can be conveyed using the graphical icons associated with State 3. For example, control circuits 120, invoking programs 112, can access files 114 and determine the STATE associated with the generated sleep episode score (i.e., 94%), determine the unique graphical icons for the 12-year-old user that are associated with STATE 3, display the determined unique graphical icons synchronously via device 118, and thereby visually convey the generated sleep episode score.

Figure 2:
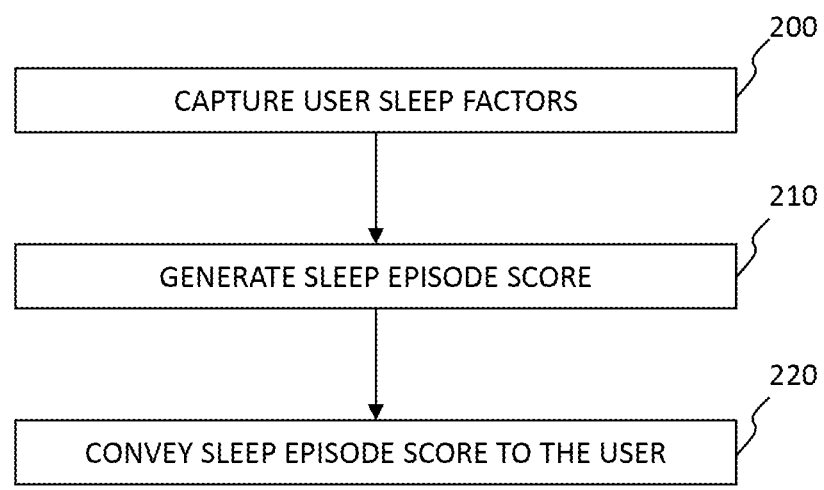
FIG. 2 is a flowchart of an exemplary process of conveying sleep factors to users, in accordance with several embodiments.

FIG. 2 is a flowchart of an exemplary process of conveying sleep factors to users, in accordance with several embodiments. Program 112 captures user sleep factors (step 200). Program 112 generates a sleep episode score (step 210). Program 112 conveys the generated sleep episode score to the user (step 220).

FIG. 3 illustrates an exemplary system 300 that may be used in accordance with this disclosure. The system 300 may comprise a control circuit or processor module 312, memory 314, and one or more communication links, paths, buses or the like 318. Some embodiments may include one or more user interfaces 316, and/or one or more internal and/or external power sources or supplies 340. The control circuit 312 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, decisions, programs, content, listings, services, interfaces, logging, reporting, etc. Further, in some embodiments, the control circuit 312 can be part of control circuitry and/or a control system 310, which may be implemented through one or more processors with access to one or more memory 314 that can store instructions, code and the like that is implemented by the control circuit and/or processors to implement intended functionality. In some applications, the control circuit and/or memory may be distributed over a communications network (e.g., LAN, WAN, Internet) providing distributed and/or redundant processing and functionality. Again, the system 300 may be used to implement one or more of the above or below, or parts of, components, circuits, systems, processes and the like.

The user interface 316 can allow a user to interact with the system 300 and receive information through the system. In some instances, the user interface 316 includes a display 322 and/or one or more user inputs 324, such as buttons, touch screen, track ball, keyboard, mouse, etc., which can be part of or wired or wirelessly coupled with the system 300. Typically, the system 300 further includes one or more communication interfaces, ports, transceivers 320 and the like allowing the system 300 to communicate over a communication bus, a distributed computer and/or communication network 130 (e.g., a local area network (LAN), the Internet, wide area network (WAN), etc.), communication link 318, other networks or communication channels with other devices and/or other such communications or combination of two or more of such communication methods. Further the transceiver 320 can be configured for wired, wireless, optical, fiber optical cable, satellite, or other such communication configurations or combinations of two or more of such communications. Some embodiments include one or more input/output (I/O) ports 334 that allow one or more devices to couple with the system 300. The I/O ports can be substantially any relevant port or combinations of ports, such as but not limited to USB, Ethernet, or other such ports. The I/O interface 334 can be configured to allow wired and/or wireless communication coupling to external components. For example, the I/O interface can provide wired communication and/or wireless communication (e.g., Wi-Fi, Bluetooth, cellular, RF, and/or other such wireless communication), and in some instances may include any known wired and/or wireless interfacing device, circuit and/or connecting device, such as but not limited to one or more transmitters, receivers, transceivers, or combination of two or more of such devices.

In some embodiments, the system may include one or more sensors 326 to provide information to the system and/or sensor information that is communicated to another component, such as the central control system, a delivery vehicle, etc. The sensors can include substantially any relevant sensor, such as distance measurement sensors (e.g., optical units, sound/ultrasound units, etc.), cameras, motion sensors, inertial sensors, accelerometers, impact sensors, pressure sensors, and other such sensors. The foregoing examples are intended to be illustrative and are not intended to convey an exhaustive listing of all possible sensors. Instead, it will be understood that these teachings will accommodate sensing any of a wide variety of circumstances in a given application setting.

The system 300 comprises an example of a control and/or processor-based system with the control circuit 312. Again, the control circuit 312 can be implemented through one or more processors, controllers, central processing units, logic, software and the like. Further, in some implementations the control circuit 312 may provide multiprocessor functionality.

The memory 314, which can be accessed by the control circuit 312, typically includes one or more processor readable and/or computer readable media accessed by at least the control circuit 312, and can include volatile and/or nonvolatile media, such as RAM, ROM, EEPROM, flash memory and/or other memory technology. Further, the memory 314 is shown as internal to the control system 310; however, the memory 314 can be internal, external or a combination of internal and external memory. Similarly, some or all of the memory 314 can be internal, external or a combination of internal and external memory of the control circuit 312. The external memory can be substantially any relevant memory such as, but not limited to, solid-state storage devices or drives, hard drive, one or more of universal serial bus (USB) stick or drive, flash memory secure digital (SD) card, other memory cards, and other such memory or combinations of two or more of such memory, and some or all of the memory may be distributed at multiple locations over the computer network 130. The memory 314 can store code, software, executables, scripts, data, content, lists, programming, programs, log or history data, user information, customer information, product information, and the like. While FIG. 3 illustrates the various components being coupled together via a bus, it is understood that the various components may actually be coupled to the control circuit and/or one or more other components directly.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system comprising:
a display;
a sensor configured to collect information associated with a sleep episode of a user;
a database configured to store a plurality of graphical icons, which are generated based on an image of the user, in association with a plurality of sleep episode scores, and a second sleep factor which is associated with the sleep episode and defined by the user; and
a control circuit in communication with the database and the sensor and configured to:
generate a first sleep factor based at least in part on the information collected by the sensor associated with the sleep episode;
determine, using the first sleep factor and the second sleep factor, a user sleep episode score; and
effect conveyance of the user sleep episode score to the user via displaying the plurality of graphical icons as a graphical representation of the user on the display,
wherein the plurality of sleep episode scores comprises:
a first sleep episode score associated with a first plurality of graphical icons configured to visually convey a first state of the user that reflects the first sleep episode score among the plurality of graphical icons, and
a second sleep episode score associated with a second plurality of graphical icons configured to visually convey a second state of the user that reflects the second sleep episode score among the plurality of graphical icons, and
wherein the control circuit is further configured to:
based on the determining the user sleep episode score as the first sleep episode score, control the display to convey the user sleep episode score by successively displaying the first plurality of graphical icons, thereby visually conveying the first state of the user, and
based on the determining the user sleep episode score as the second sleep episode score, control the display to convey the user sleep episode score by displaying the second plurality of graphical icons, thereby visually conveying the second state of the user.

2. The system of claim 1, wherein the control circuit is further configured to generate, using at least one of the first sleep factor or the second sleep factor, a suggestion for improving the user sleep episode score.

3. The system of claim 1, wherein the control circuit is further configured to generate the first sleep factor at a predetermined time interval.

4. The system of claim 1, wherein the control circuit is further configured to generate the first sleep factor based on the user being positioned proximate to a predetermined sleep structure.

5. The system of claim 1, wherein the control circuit is further configured to determine, via sensor data from the sensor, a sleep cycle associated with the sleep episode.

6. The system of claim 1, wherein the control circuit is further configured to generate the first sleep factor based at least in part on at least one of a heart rate measurement, accelerometer data, a blood pressure measurement, an ambient light measurement, an ambient noise measurement, an ambient temperature measurement, or combinations thereof.

7. The system of claim 1, wherein the second sleep factor is associated with one or more of a past experience of the user, a current experience of the user, a psychopathologic symptom of the user, and a sleep-related ecological momentary assessment.

8. The system of claim 1, wherein the second sleep factor is based on user sleep log data comprising at least one of desired wake times, desired sleep times, environmental disturbances, mental alertness characterizations, ingested pharmaceuticals associated with one or more sleep episodes, perceived stress information, or perceived causes of nocturnal disturbances.

9. The system of claim 1, wherein the control circuit is further configured to:
based on the determining the user sleep episode score as the first sleep episode score, control the display to display the first plurality of graphical icons as a visual animation of the first state of the user, and based on the determining the user sleep episode score as the second sleep episode score, control the display to display the second plurality of graphical icons as a visual animation of the second state of the user.

10. A method comprising:

generating a first sleep factor based on information about a sleep episode of a user that is collected by a sensor;

storing a plurality of graphical icons, which are generated based on an image of the user, in association with a plurality of sleep episode scores;

generating a second sleep factor based on receipt of information from the user;

determining, via a control circuit, a user sleep episode score using the first sleep factor and the second sleep factor;

effecting conveyance, via the control circuit, of the user sleep episode score to the user via displaying the plurality of graphical icons as a graphical representation of the user on a display, wherein the plurality of sleep episode scores includes:

a first sleep episode score associated with a first plurality of graphical icons configured to visually convey a first state of the user that reflects the first sleep episode score among the plurality of graphical icons, and a second sleep episode score associated with a second plurality of graphical icons configured to visually convey a second state of the user that reflects the second sleep episode score among the plurality of graphical icons, and wherein the effecting the conveyance further comprises:

based on the determining the user sleep episode score as the first sleep episode score, controlling the display to convey the user sleep episode score by successively displaying the first plurality of graphical icons, thereby visually conveying the first state of the user, and based on the determining the user sleep episode score as the second sleep episode score, controlling the display to convey the user sleep episode score by displaying the second plurality of graphical icons, thereby visually conveying the second state of the user.

11. The method of claim 10, further comprising generating, via the control circuit, a suggestion for improving the user sleep episode score using at least one of the first sleep factor or the second sleep factor.

12. The method of claim 10, wherein the generating the first sleep factor further comprises generating the first sleep factor using data captured by the sensor at predetermined time intervals.

13. The method of claim 10, wherein the generating the first sleep factor further comprises generating the first sleep factor using data captured by the sensor based on the user being positioned proximate to a predetermined sleep structure.

14. The method of claim 10, wherein the generating the first sleep factor further comprises generating the first sleep factor using a sleep cycle measurement.

15. The method of claim 10, wherein the generating the first sleep factor further comprises generating the first sleep factor using at least one of heart rate measurements, accelerometer data, a blood pressure measurement, an ambient light measurement, an ambient noise measurement, an ambient temperature measurement, or combinations thereof.

16. The method of claim 10, further comprising setting the second sleep factor based at least in part on at least one of a past experience of the user, a current experience of the user, a psychopathologic symptom of the user, a sleep-related ecological momentary assessment, or combinations thereof.

17. The method of claim 10, wherein the second sleep factor is based on user sleep log data comprising at least one of desired wake times, desired sleep times, environmental disturbances, mental alertness characterizations, ingested pharmaceuticals associated with one or more sleep episodes, perceived stress information, or perceived causes of nocturnal disturbances.

* * * * *